United States Patent [19]

McCandlish et al.

[11] Patent Number: 4,476,102
[45] Date of Patent: * Oct. 9, 1984

[54] MOLYBDENUM OXYCARBONITRIDE COMPOSITIONS AND PROCESS FOR PREPARING THE SAME

[75] Inventors: Larry E. McCandlish, Highland Park; Larissa W. Turaew, Fairlawn, both of N.J.

[73] Assignee: Exxon Research and Engineering Co., Florham Park, N.J.

[*] Notice: The portion of the term of this patent subsequent to Jan. 17, 2001 has been disclaimed.

[21] Appl. No.: 209,998

[22] Filed: Nov. 24, 1980

[51] Int. Cl.$^3$ .................................................. C01C 3/00
[52] U.S. Cl. ........................................ 423/365; 51/293; 51/309; 75/238; 501/87; 501/96; 501/98
[58] Field of Search ...................... 106/43, 55; 423/365, 423/409; 501/87, 96; 51/307, 309, 293; 252/438; 75/238; 428/627, 932

[56] References Cited

U.S. PATENT DOCUMENTS

| | | | |
|---|---|---|---|
| 3,415,760 | 12/1968 | Hadley et al. | 252/438 |
| 3,492,100 | 1/1970 | Roubin et al. | 423/365 X |
| 3,872,136 | 3/1975 | Middelhock | 423/317 |
| 4,239,536 | 12/1980 | Yamamoto et al. | 75/238 |

FOREIGN PATENT DOCUMENTS

| | | | |
|---|---|---|---|
| 10692 | 2/1978 | Japan . | |
| 54-034719 | 10/1979 | Japan | 428/647 |
| 55-31517 | 3/1980 | Japan | 106/43 |

OTHER PUBLICATIONS

Grant Julius editor, *Hackh's Chemical Dictionary*, McGraw–Hill Book Company, New York, 1969, p. 35.
Izv. Akad, Navk, SSSR Neorg Mata. 1976, 12(a), 1581–1584.

Primary Examiner—John Doll
Assistant Examiner—Jackson Leeds
Attorney, Agent, or Firm—Robert J. North; Edward H. Mazer

[57] ABSTRACT

Novel molybdenum oxycarbonitride compositions are described together with a general method of synthesis. The compositions can be obtained by the relatively low temperature thermal decomposition of an amine molybdate and can be amorphous, poorly crystalline, or substantially crystalline, and can unexpectedly possess high surface areas in the region of about 130 m$^2$/g and higher. The compositions have the general formula: $MoO_aC_bN_c$, where a, b and c are non-zero decimal values and the sum: a+b+c, is less than or equal to about one, as evidenced by X-ray diffraction and chemical analyses. The compositions are useful as abrasives, as for removing oxide coatings from metals.

11 Claims, 3 Drawing Figures

● = metal atom

○ = heteroatom

● = metal atom
○ = heteroatom

MOLYBDENUM OXYCARBONITRIDE COMPOSITIONS AND PROCESS FOR PREPARING THE SAME

BACKGROUND OF THE INVENTION

1. Field of the Invention

This invention relates to a new composition of matter, molybdenum oxycarbonitride, a general method for its preparation, and its utility as an abrasive.

2. Brief Description of the Prior Art

In the area of abrasives, new compositions are constantly being evaluated in an attempt to discover new and more efficient materials for use in metal-sanding and finishing. Already known in the art are carbides, such as tungsten and molybdenum carbides, various oxycarbides and carbonitrides of Group VIA metals. In addition, several general references to oxycarbonitrides of Group VIA metals are also known in the art.

U.S. Pat. No. 3,492,100 (1970) describes the general preparation of oxycarbonitrides and carbonitrides of metals from Group IVa, Va, and mixed metal oxycarbonitrides and carbonitrides of Group VIa metals. Particularly described are those of titanium, zirconium, vanadium, niobium, and tantalum.

Japanese Kokai No. 10,692 (1978) describes coated hard alloys for cutting tools comprising an intermediate layer of a Group IVa, Va or VIa oxycarbonitride.

U.S. Pat. No. 3,872,136 (1975) discloses a process for the preparation of vanadium carbonitride, vanadium oxycarbide or vanadium oxycarbonitride from other vanadium compounds.

The reference Izv. Akad. Nauk. SSSR, Neorg. Mater. 1976, 12(9), 1581-4, describes cubic oxycarbonitrides of Ti and Zn and methods of preparation.

However, the above-described references do not refer specifically to the composition of molybdenum oxycarbonitride, or to a specific method for its preparation.

SUMMARY OF THE INVENTION

We have unexpectedly found that molybdenum oxycarbonitride, a new composition of matter, can be synthesized by the thermal decomposition of an amine molybdate, in a non-oxidizing and preferably reducing atmosphere. The composition can be obtained possessing abrasive properties and very high surface areas, on the order of 60–130 m$^2$/g. (as measured by standard argon-BET methods) and can be pyrophoric at room temperature. The material can readily be passivated for use under ambient conditions.

In accordance with this invention there is provided a composition comprising molybdenum oxycarbonitride. The composition can be amorphous, poorly crystalline or substantially crystalline, and has the general formula: $MoO_aC_bN_c$, wherein a, b and c are non-zero decimal values, and wherein the sum: a+b+c, is less than or equal to about one.

Also provided is a process for preparing the subject composition comprising the step of thermally decomposing an amine molybdate at elevated temperature in the presence of a nonoxidizing atmosphere, wherein said amine contains at least one single bond C—N grouping.

A preferred process is where the amine molybdate is ethylenediammonium molybdate and is thermally decomposed at a temperature above about 200° C., preferably about 500° C., in an inert atmosphere, such as helium. Further provided is an abrasive composition comprising molybdenum oxycarbonitride.

BRIEF DESCRIPTION OF THE FIGURES

FIG. 1 depicts comparative X-ray powder diffraction patterns on the same scale of:

(A) pyrophoric molybdenum oxycarbonitride (under Kapton film) obtained by the thermal decomposition of ethylenediammonium molybdate in a helium atmosphere at about 650° C., and (B) passivated molybdenum oxycarbonitride, obtained by contacting the pyrophoric form at room temperature with an atmosphere of oxygen/helium. Also illustrated are the peak indices based on the standard cubic unit cell.

Figure 2:
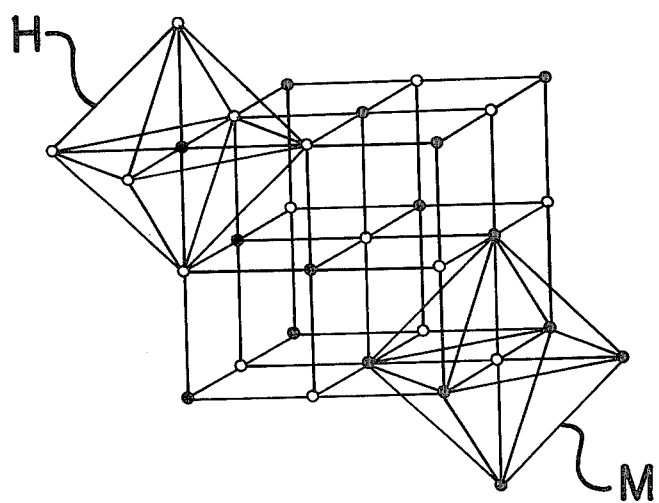

FIG. 2 is a schematic representation of the face-centered cubic molybdenum oxycarbonitride crystal structure, illustrating the metal atom (M) and heteroatom (H) substructures.

Figure 3:
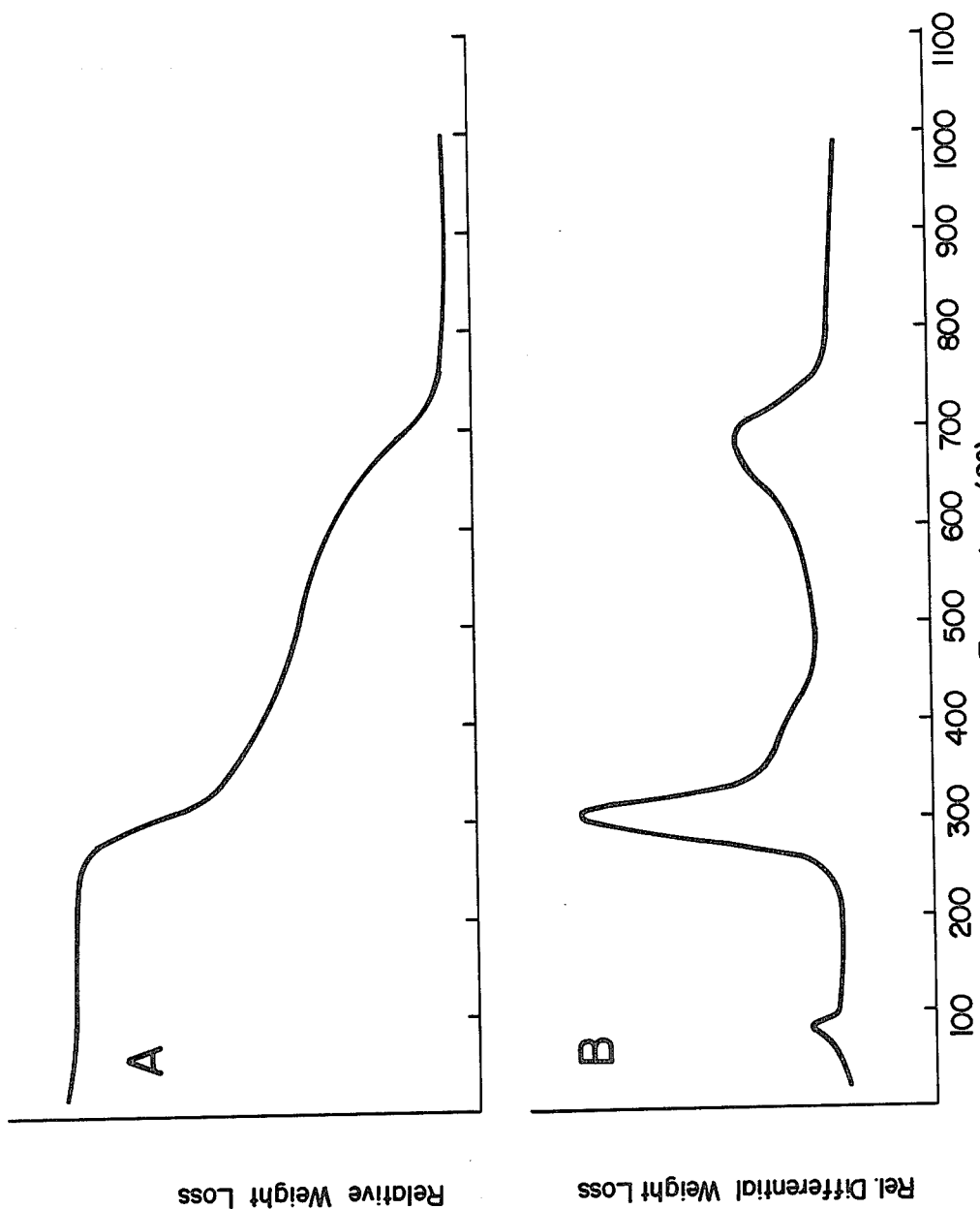

FIG. 3 depicts a thermogram (A) and its derivitive (B) illustrating the decomposition of an ethylene-diamine adduct of molybdic acid to molybdenum oxycarbonitride as obtained by thermogravimetric analysis.

DESCRIPTION OF THE INVENTION AND PREFERRED EMBODIMENTS

The subject composition, molybdenum oxycarbonitride belongs to a general class of materials including interstitial carbides and nitrides which because of their physical nature are often not capable of being precisely defined in terms of unique compositional properties as are for example, organic compounds. Interstitial carbides and nitrides, as a class, are generally comprised of two interpenetrating substructures: a metal atom substructure and a heteroatom substructure. The metal atom substructure dominates X-ray scattering, predominately determines the X-ray diffraction pattern, and forms a polyhedral array within which the heteroatoms occupy certain positions in the polyhedral interstices, for example as depicted in FIG. 2. Generally, the metal atom substructure in this class of materials differs from the metal atom arrangement in the pure metal, which is usually evidenced by a difference in the X-ray powder diffraction patterns of the materials. However, usually in both cases there is a periodic ordering of the metal atoms. By contrast, the heteroatom substructure may or may not exhibit a periodic ordering and as a further complicating factor, can in general accommodate a varying number of heteroatoms vacancies. Thus, materials in this class of compounds generally exhibit non-stoichiometry with respect to the number of heteroatoms in the interstitial substructure which renders precise definition of the heteroatom substructure very difficult. Further, several different metal atom substructure arrangements are possible for a given empirical formula. Consequently, this class of materials usually exhibits complex phase diagrams, for example, as is known for molybdenum carbide and tungsten carbide. Thus, precise and complete structural characterization of this class of materials is a difficult task since the materials in addition to their non-stoichiometric nature, may also be air-sensitive, pyrophoric, high-melting, and insoluble in standard organic solvents.

With the above discussion as a background, analysis by X-ray diffraction, elemental analysis and thermogravimetric analysis, indicates that the metal atom substructure of molybdenum oxycarbonitride prepared by the process described herein is reasonably believed to be represented as a face cubic-centered lattice as illustrated in FIG. 2. Within the face-centered cubic structure of molybdenum oxycarbonitride as illustrated in FIG. 2, it is believed that each heteroatom site is surrounded by six molybdenum atoms while each molybdenum atom, in turn, is surrounded by six heteroatom sites. Thus, the ratio of the number of the heteroatom sites to the number of molybdenum atoms is ideally 1:1. Assuming a random distribution for oxygen, carbon and nitrogen atoms, as well as complete occupancy of all heteroatom sites in the heteroatom substructure, leads to the ideal empirical formula for the composition: $MoO_{\frac{1}{3}}C_{\frac{1}{3}}N_{\frac{1}{3}}$. However, since the material can probably support a varying number of heteroatom vacancies within the heteroatom substructure as discussed above, and furthermore, since the ratio of O:C:N atoms, during synthesis would not be expected to be incorporated in exactly a 1:1:1 ratio, it follows that elemental analysis indicates only a general overall heteroatom content and that the ratio of O:C:N will vary to a great extent in the composition.

Within this context, the formula of the novel composition is $MoO_aC_bN_c$, where a, b and c are non-zero decimal values and the sum: a+b+c, due to non-stoichiometry and difficulty in exact measurement, is less than or equal to about one. (The sum of one being the ideal case under the conditions of exact measurement and complete occupancy of the heteroatom sites). The ranges for the individual decimal values of a, b and c can vary then as described above with the proviso that each individual value is greater than zero and the sum: a+b+c, is not greater than about one for the pure composition.

Figure 1:
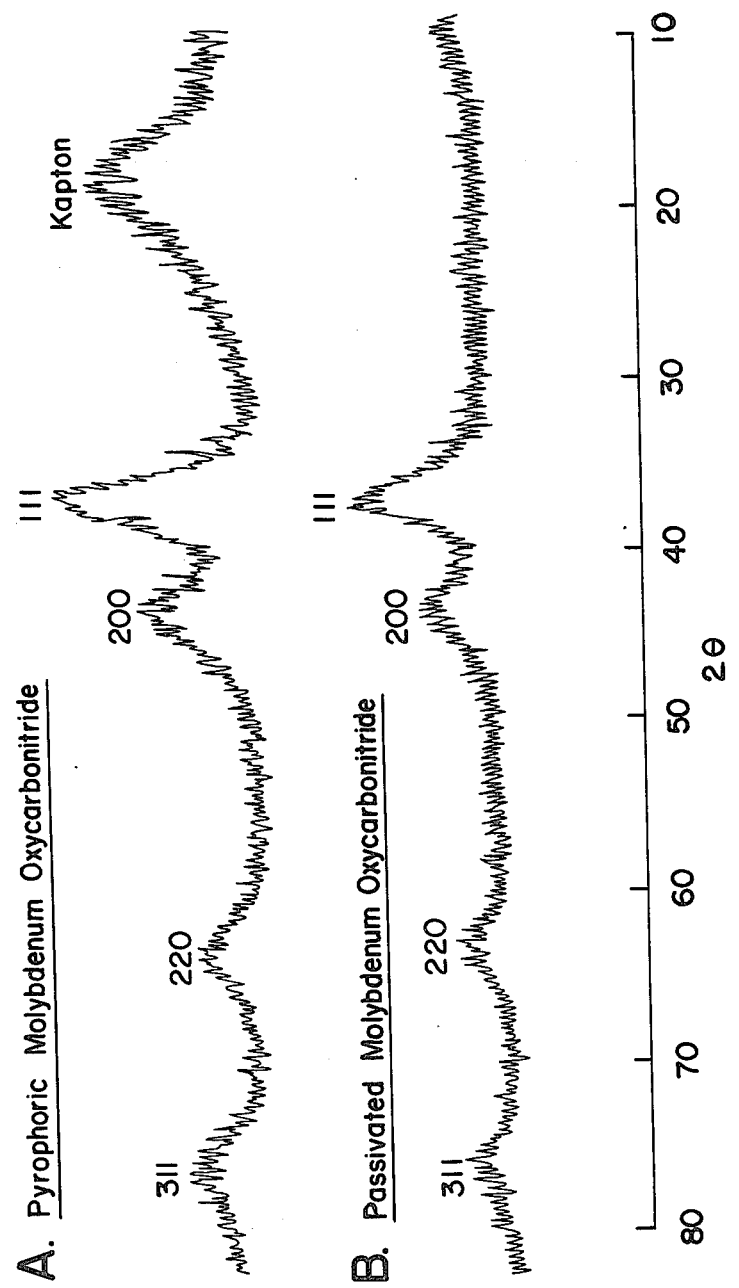

A particular example, described herein, is $MoO_{0.43}C_{0.31}N_{0.33}$, prepared by the decomposition of ethylenediammonium molybdate, whose X-ray diffraction pattern is illustrated in FIG. 1.

Molybdenum oxycarbonitride is generally pyrophoric when freshly prepared by the process described herein and in order to stabilize the material for use as an abrasive it is usually necessary to passivate it by surface oxidation at room temperature by conventional techniques. For example, the passivating step can be conducted by contacting the pyrophoric material with a stream of oxygen/helium at room temperature. The material in the passivated phase is now usable as an abrasive for removing metal oxides and films from metal surfaces, as for example, aluminum oxide from air-exposed aluminum surfaces.

Generally, the passivated material is incorporated into a conventional liquid vehicle, such as methanol or hydrocarbon lubricant by grinding or mixing to form a suitable paste.

The above-described composition can be passivated by contacting the pyrophoric material with a stream of oxygen/helium at room temperature in stages of increasing oxygen concentration from about 2 to 10 volume percent or higher, to yield, for example, $MoO_{0.99}C_{0.31}N_{0.33}$, whose X-ray diffraction pattern is illustrated in FIG. 1(B). This material can be incorporated into methanol for use as an abrasive. Thus, passivated molybdenum oxycarbonitride is also deemed to be within the scope of the instant composition as well as molybdenum oxycarbonitride compositions including other impurities which may also be present.

X-ray diffraction analysis (see FIG. 1) also is consistent with the high surface areas of the obtained composition. Surface areas, as measured by the well-known argon BET method, can be on the order of about 10 to 130 $m^2/g$ and higher and this is evidenced by relatively wide peak half-widths in the X-ray diffraction pattern of FIG. 1(A). Here, a crystallite size of about 30-40 Angstroms is inferred from the observed half-widths.

The composition can exist in amorphous, poorly crystalline, or crystalline forms which can be evidenced by their respective X-ray diffraction patterns.

By the term "amorphous" is meant an X-ray diffraction pattern exhibiting essentially a straight line. By the term "poorly crystalline" is meant an X-ray diffraction pattern exhibiting distinct yet broad scattering peaks, as depicted in FIG. 1-A. By the term "crystalline" is meant an X-ray diffraction pattern exhibiting very sharp scattering peaks. In general, large particle size crystalline materials exhibit narrow diffraction lines and amorphous materials exhibit very broad diffraction lines.

Molybdenum oxycarbonitride prepared by the process described herein is generally a black powder, having a very high melting point, is extremely insoluble in common organic solvents, is air and water-sensitive, generally has a crystallographic density of about 8.0-10.1 $g/cm^3$, and is usually pyrophoric at room temperatures. The lattice parameters exhibited by poorly crystalline molybdenum oxycarbonitride, prepared by the preferred process is in the range of about 4.1 to 4.4 Angstroms and can be influenced by the particular atmosphere used as described below.

Also a subject of this invention is a process for preparing the subject composition. Generally, the process comprises thermally decomposing an amine molybdate at elevated temperature, under a non-oxidizing atmosphere, preferably a reducing atmosphere, wherein said amine contains at least one single bond C—N grouping, and recovering the resulting molybdenum oxycarbonitride.

By the term "molybdate" as used herein is meant molybdates, polyoxomolybdates, including those formed from molybdic acids, oxides and acid anhydrides, of the formulas: $MoO_3 \cdot xH_2O$, $H_2MoO_4$, $H_2Mo_2O_7$, $H_2Mo_3O_{10}$, $H_6Mo_7O_{24}$, $H_4Mo_8O_{26}$ and the like.

By the term "amine molybdate" as used herein, is meant a compound, salt, complex or adduct formed between the interaction of an amine and respective molybdic acid, oxide or anhydride as described herein.

Amines that are operable in this invention are alkyl amines, alkylenediamines and aromatic amines that preferably contain 1-20 carbon atoms and contain at least one single bond C—N grouping. The reason why this structural limitation is necessary in the process is not clear. One theory that we do not wish to be bound by is that the single bond C—N grouping enables both the carbon and nitrogen fragments of the amine to be simultaneously incorporated upon decomposition into the final oxycarbonitride. Thus, pyridine and ammonia are inoperable as the amine components of the amine molybdate in the process, whereas 4-ethylaminopyridine and ethylamine are operable amine components.

The alkylamines and alkylenediamines may be linear or branched and may also contain substituents which are inert under the reaction conditions, e.g., alkoxy or halogen. The aromatic amines may also contain substituents on the aromatic ring which are inert under the reaction conditions, e.g., alkoxy or halogen.

Representative examples include ethylenediamine, butylamine, ethylamine, diethylamine, di-n-butylamine, trimethylamine, triethylamine, 1,3-cyclohexane bismethylamine, aniline, 4-ethylaminopyridine and the like and mixtures thereof. A preferred amine in the process is ethylenediamine.

The amine molybdate is treated in the process by subjecting the compound to a temperature sufficient to cause thermal decomposition. By the term "thermal decomposition" is meant the process of thermal rearrangement of the compound involving usually carbon-carbon, carbon-nitrogen, molybdenum-oxygen and also carbon-hydrogen bond breaking, thereby resulting in molybdenum oxycarbonitride. Temperatures at which thermal decomposition of the operable amine molybdate occurs depends upon the particular amine molybdate employed and is usually in the range of about 150° to 800° C., preferably about 300° to 700° C., and particularly preferred about 500°–600° C.

The thermal decomposition is conducted under a non-oxidizing atmosphere, which can be inert and/or reducing in nature, preferably reducing, and includes hydrogen, carbon monoxide, helium and the like, and mixtures thereof. In the process there is preferably a substantial absence of elemental oxygen and water at temperatures above 150° C. during thermal decomposition.

We have found that in the case of ethylenediammonium molybdate, the compound can be thermally decomposed if desired in an atmosphere substantially comprising helium, exclusively. However, with other amine molybdates at atmosphere containing some hydrogen gas is usually necessary. Preferably, a small amount of hydrogen gas is used to counteract small traces of oxygen or moisture which may be present in the process atmosphere. The process atmosphere preferably contains about 25–50 volume % $H_2$ in admixture with helium or carbon dioxide.

The process atmosphere can be maintained at atmospheric pressure, under reduced pressure, or greater than atmospheric pressure. Preferably the thermal decomposition is conducted at atmospheric pressure. The process atmosphere can be continuous and dynamic as in a constant flowing stream or used in a tube furnace or can be a static atmosphere as present in an autoclave. Preferred is a constant flowing stream of the atmospheric gaseous mixture.

Space velocity of the inert/reducing gas in a flowing, dynamic atmosphere is not critical and can be conveniently conducted in the range of about 100 to 50,000 v/v/hr. What is important is that the flow of gas should be sufficient to sweep away gaseous by-products from the reaction zone and to maintain a sufficiently high concentration of reducing atmosphere in the vicinity of the amine molybdate.

Apparatus for carrying out the thermal decomposition may be any conventional type known to those skilled in the art and include stainless steel and glass tube furnaces, autoclaves, and the like.

The following examples are illustrative of carrying out the best mode of the invention as contemplated by us and should not be construed as being limitations on the scope and spirit of the instant invention.

EXAMPLE 1

Preparation of Ethylenediammonium Molybdate 50 g of molybdic acid, $H_2MoO_4$, and 750 ml of pure ethylenediamine were refluxed under stirring for about 16 hours. The resulting white-colored solid was collected on a fritted funnel washed with ethanol to remove any unreacted ethylenediamine and then dried in an oven to remove the ethanol. Obtained was a white solid having the following elemental analysis: % N, calculated 12.6, found 13.99; % Mo, calculated 43.2, found 46.9. The above-described preparation was found to be reproducible.

THERMAL DECOMPOSITION

Thermal decomposition of the above-described ethyleneammonium molybdate was carried out by preheating a glass tube furnace at about 650° C., through which a stream of helium was flowing at 600 ml/min. The above-prepared sample was placed into a quartz boat which was then placed into the tube furnace. The temperature was allowed to equilibrate for about 5 minutes and then the sample was heated to 650° C., under the helium atmosphere, for about 20 minutes to effect the decomposition. Subsequently, the tube was allowed to cool to room temperature, and the tube was then flushed with helium gas for about 15 minutes. Obtained was a black, pyrophoric material which had the approximate composition: $MoO_{0.43}C_{0.31}N_{0.33}$. The pyrophoric material was passivated by contacting the solid at room temperature with a gaseous mixture of oxygen and helium containing increasing concentrations of oxygen according to the following schedule:

| Feedstream | Time |
| --- | --- |
| 2% $O_2$/He | 1 hour |
| 4% $O_2$/He | 1 hour |
| 6% $O_2$/He | 1 hour |
| 10% $O_2$/He | 1 hour |

The resulting composition has the empirical formula: $MoO_{0.99}C_{0.31}N_{0.33}$ based on results of the chemical analysis: Mo, 79.77%; O, 13.16%; C, 3.05%; N, 3.79%; H, 0.42%. X-ray analysis showed that in the pyrophoric material, the molybdenum atoms form a cubic closest packed array. Thus, the empirical formula $MoO_{0.43}C_{0.31}N_{0.33}$, indicates that all octahedral interstices are occupied by O, C and N atoms, respectively, $(0.43+0.31+0.33=1.07)$. X-ray line broadening techniques revealed that the passivated material had an average particle size of about 30 Angstroms (Å).

Carrying out the thermal decomposition in carbon monoxide, rather than helium, at 650° C., resulted in a material exhibiting the same face-centered-cubic lattice, but having a significantly larger lattice constant, being 4.21Å versus 4.13Å. The largest lattice constant, 4.32Å, was obtained using a reducing atmosphere comprising helium/carbon monoxide mixture.

EXAMPLE 2

The following described experiments were conducted to illustrate the reversibility of the passivated and surface active crystalline forms of the above-described oxycarbonitride.

A. The passivated material described in Example 1 was treated at 450° C. with a stream of hydrogen for 0.5 hour. The resulting pyrophoric black solid had a surface area of about 135 $m^2/g$ (as measured by standard BET method).

B. The resulting material from A above was passivated by the procedure described in Example 1 resulting in a passivated material having an argon BET surface area of about 98 $m^2/g$.

C. The resulting material from B above was treated with a stream of $H_2$ at 450° C. for 0.5 hours resulting in a pyrophoric black powder having a BET surface area of about 131 m²/g.

EXAMPLE 3

Ethylenediammonium molybdate prepared as in Example 1 was thermally decomposed in the tube furnace described in Example 1, at 350° C. with a stream of helium (600 ml/min.) for 1.5 hours. The resulting black solid had an argon BET surface area of about 18 m²/g and the X-ray diffraction pattern indicated the solid was "amorphous" molybdenum oxycarbonitride.

EXAMPLE 4

Following the general procedure outline in Example 1, the following amine molybdates, prepared from molybdic acid ($H_2MoO_4$), were thermally decomposed to yield molybdenum oxycarbonitride. Exact conditions used are listed in Table I. Each of the materials was passivated after formation according to the procedure described in Example 1.

TABLE I

| Amine Molybdate | Temp. | Atmosphere[a] | Time |
|---|---|---|---|
| (1) 1,3-cyclohexane-bis-methylamine | 400° C. | 75/25 $H_2$/He | 20 min. |
| (2) trimethylamine | 400° C. | 100% $H_2$ | 20 min. |
| (3) di-n-butylamine | 400° C. | 75/25 $H_2$/He | 20 min. |
| (4) aniline | 400° C. | 75/25 $H_2$/He | 20 min. |
| (5) dimethylamine | 400° C. | 50/50 $H_2$/He | 20 min. |
| (6) ethylamine | 400° C. | 50/50 $H_2$/He | 20 min. |

[a]flow rate of 600 ml/min.

X-ray diffraction analyses indicated that molybdenum oxycarbonitride was formed in each of the above cases.

COMPARATIVE EXAMPLE 1

Ammonium molybdate (commercially available) was thermally treated following the general procedure described in Example 1 in a 1:1 CO/$H_2$ flowing atmosphere at 500° C. Analysis by X-ray diffraction of the obtained solid indicated that it was not molybdenum oxycarbonitride.

COMPARATIVE EXAMPLE 2

A pyridine salt of molybdic acid (prepared by refluxing a mixture of molybdic acid and pyridine) was thermally treated in an argon atmosphere at 400° C. according to the general procedure described in Example 1. Analysis by X-ray diffraction of the obtained solid indicated that it was not molybdenum oxycarbonitride.

EXAMPLE 5

Molybdenum oxycarbonitride powder (prepared as in Example 1) was converted to an abrasive paste by the addition of methanol as a carrying vehicle. The paste was applied to the surface of a heavily air oxidized aluminum plate, and vigorous polishing resulted in the removal of the corrosion producing a shiny aluminum surface.

What is claimed is:

1. A composition of matter consisting essentially of molybdenum oxycarbonitride, possessing a face-centered cubic structure, as evidenced by powder X-ray diffractometry and elemental analysis, said composition having interstitial oxygen, carbon and nitrogen atoms distributed throughout the bulk structure.

2. The composition of matter of claim 1 being of the formula: Mo $O_a$ $C_b$ $N_c$ where a, b and c are non-zero decimal values, and wherein the sum: a+b+c, is less than or equal to about 1.

3. The composition of matter of claim 2 being of the formula: Mo $O_{0.43}$ $C_{0.31}$ $N_{0.33}$.

4. The composition of matter of claim 1 possessing an argon BET surface area of about 60 square meters per gram and higher.

5. The composition of matter of claim 1 being passivated with oxygen.

6. A process for producing the composition of claim 1 comprising the step of thermally decomposing an amine molybdate at elevated temperature sufficient to form said composition in the presence of a nonoxidizing atmosphere wherein said amine contains at least one single bond C—N grouping.

7. The process of claim 6 wherein said thermal decomposition is conducted at a temperature in the range of up to 800° C.

8. The process of claim 6 wherein said atmosphere comprises hydrogen, helium, carbon monoxide, or mixture thereof.

9. The process of claim 6 wherein said amine is an alkylamine, alkylenediamine or aromatic amine containing 1 to 20 carbon atoms.

10. The process of claim 9 wherein said amine is ethylamine, diethylamine, butylamine, ethylenediamine, di-(n-butyl) amine, trimethylamine, triethylamine and 1,3-cyclohexane bis(methylamine).

11. A process for producing the composition of claim 1 comprising the step of thermally decomposing ethylenediammonium molybdate at an elevated temperature sufficient to form said composition, said temperature being up to 700° C. wherein the thermal decomposition is conducted in the presence of an atmosphere substantially comprising helium.

* * * * *